(12) United States Patent
Pan

(10) Patent No.: US 7,854,901 B2
(45) Date of Patent: Dec. 21, 2010

(54) OIL-SMOKE EXTRACTOR

(76) Inventor: Gong-wei Pan, No. 5, First Rong-gui-hua-feng-sha-xi-di Road, Shunde District, Foshan City, GuangDong (CN) 528305

( * ) Notice: Subject to any disclaimer, the term of this patent is extended or adjusted under 35 U.S.C. 154(b) by 293 days.

(21) Appl. No.: 12/239,766

(22) Filed: Sep. 27, 2008

(65) Prior Publication Data

US 2009/0087350 A1 Apr. 2, 2009

(30) Foreign Application Priority Data

Sep. 30, 2007 (CN) .................... 2007 2 0057803 U

(51) Int. Cl.
*A61L 9/20* (2006.01)
(52) U.S. Cl. ........................ 422/122; 422/120; 422/121; 454/156
(58) Field of Classification Search .................... 422/28, 422/120, 121, 122, 186.3; 454/156; 96/224; 250/455.11
See application file for complete search history.

(56) References Cited

U.S. PATENT DOCUMENTS 7,327,087 B2 * 2/2008 Wang .......................... 313/635
2003/0217641 A1 * 11/2003 Palestro et al. ................ 95/273

* cited by examiner

*Primary Examiner*—Sean E Conley
(74) *Attorney, Agent, or Firm*—Moore Patents; David Dreyfuss

(57) ABSTRACT

The present invention relates to an oil-smoke extractor including a housing defining a number of air holes, a bottom plate detachably secured to the housing and a sterilization and deodorization device seated in a receiving space jointly defined by the housing and the bottom plate. The sterilization and deodorization device includes two lamp supports fixed to the front plate, a pair of lamp holders respectively secured to the lamp supports, at least one nano photocatalyst lamp disposed between the lamp holders, a sterilization lampshade fixed to the lamp supports and an axial flow fan corresponding to one of the air holes in the front plate. When the oil-smoke extractor stops running, the sterilization and deodorization device is powered and begins to work. The kitchen air flows into and out of the oil-smoke extractor via the air slots and the air holes.

8 Claims, 3 Drawing Sheets

OIL-SMOKE EXTRACTOR

CROSS-REFERENCE TO RELATED APPLICATIONS

The present invention claims priority to Chinese Patent Application No. CN 200720057803.6 filed Sep. 30, 2007, which is incorporated by reference herein in its entirety.

FIELD OF THE INVENTION

The present invention relates to oil-smoke extractors and, more particularly, to an oil-smoke extractor which can effectively kill bacteria and purify environment.

BACKGROUND OF THE INVENTION

Oil-smoke extractors are widely used in kitchens for timely extracting oil and smoke generated during cooking. An oil-smoke extractor typically includes a housing defining an opening at a lower section thereof and a bottom plate detachably secured to the housing. The housing and the bottom plate corporately encloses a receiving space for receiving an electronic motor, a wind wheel and an automatic cleaning device therein. The bottom plate is provided with a pair of pumping inlets. A top plate of the housing is provided with a discharging outlet. In operation, oil and smoke flow into the oil-smoke extractor via the pumping inlets and out of the oil-smoke extractor to the outside from the discharging outlet.

However, experiments show, although the previously described conventional oil-smoke extractor can extract most of the oil-smoke, there is still remarkable amount of residual oil and smoke remaining in the kitchen. Additionally, the adverse particulates in the oil-smoke may easily cling on the surrounding walls and surfaces of objects in the kitchen, which will inevitably lead to air pollution and breeding of bacteria in the kitchen, especially in hot humid summer.

What is needed, therefore, is to provide a new oil-smoke extractor which can overcome the disadvantages of conventional oil-smoke extractors described above.

SUMMARY OF THE INVENTION

One object of the present invention is to provide an oil-smoke extractor which can effectively kill bacteria and purify environment.

According to one embodiment of the present invention, an oil-smoke extractor includes:
a housing having a front plate, the front plate defining a number of air holes;
a bottom plate detachably assembled to the housing, the housing and the bottom plate jointly defining a receiving space; and
a sterilization and deodorization device seated in the receiving space, the sterilization and deodorization device including:
  a pair of lamp supports fixed to the front plate;
  a pair of lamp holders secured to the lamp supports, respectively;
  at least one nano photocatalyst lamp arranged between the lamp holders;
  a sterilization lampshade fixed to the lamp supports; and
  an axial flow fan positioned corresponding to one of the air holes in the front plate.

In the oil-smoke extractor in accordance with one embodiment of the present invention, when the oil-smoke extractor stops running, the axial flow fan and the at least one nano photocatalyst lamp are powered and begin to work. The kitchen air flows into and out of the oil-smoke extractor through the air holes. The nano photocatalyst lamp can effectively and quickly kill the bacteria in the kitchen air and purify the kitchen air.

Specifically, the oil-smoke extractor further includes a decorative board. The decorative board defines a number of air slots corresponding to the air holes.

Specifically, the decorative board forms a number of protrusions at upper edge thereof and defines a mounting recess at a lower edge thereof. A number of mounting slits are defined at the conjunction of the front plate and the top plate. In assembly, the lower edge of the front plate is positioned in the mounting recess and the protrusions are inserted into corresponding mounting slits.

Specifically, the at least one nano photocatalyst lamp has a wavelength of 365 nmUV. Outer surface of the lamp is coated with a layer of nano photocatalyst $TiO_2$ or is covered with a layer of glass-fiber implanted with nano photocatalyst $TiO_2$.

Other advantages and novel features will be drawn from the following detailed description of preferred embodiment with reference to the attached drawings, in which:

DETAILED DESCRIPTION OF THE INVENTION

The present invention will now be described more fully with reference to the accompanying drawings.

Figure 1:
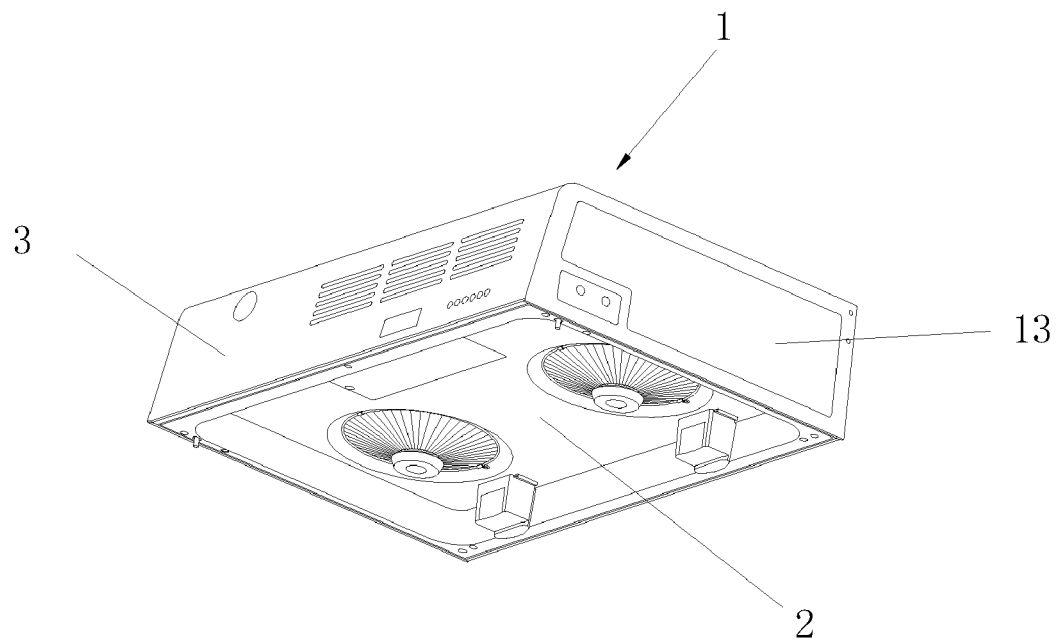
FIG. 1 depicts an isometric, perspective view of a oil-smoke extractor according to one embodiment of the present invention.
Figure 2:
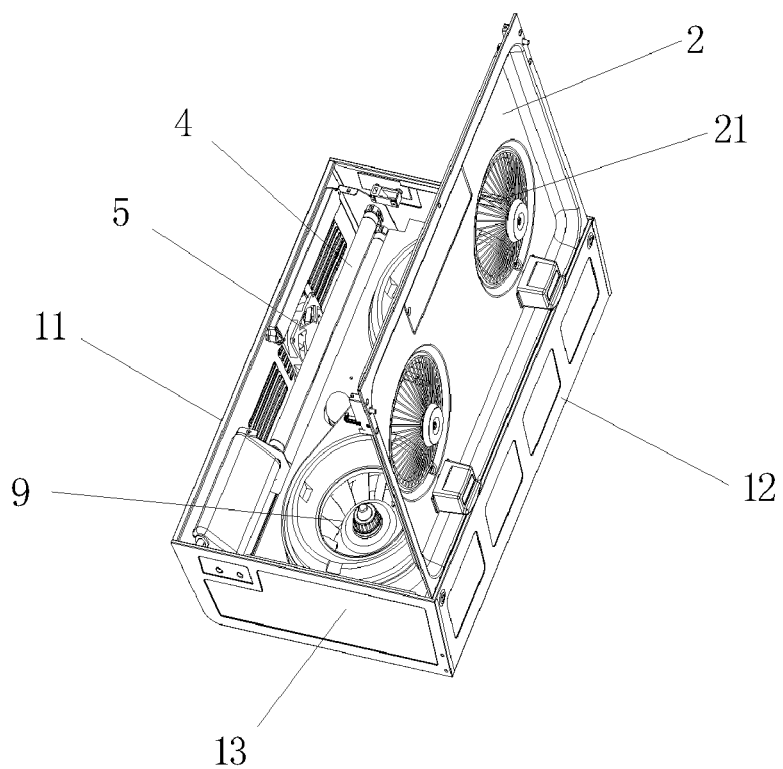
FIG. 2 depicts another isometric, perspective view of the oil-smoke extractor of FIG. 1, wherein a bottom plate of the oil-smoke extractor is set in an opening position.
Figure 3:
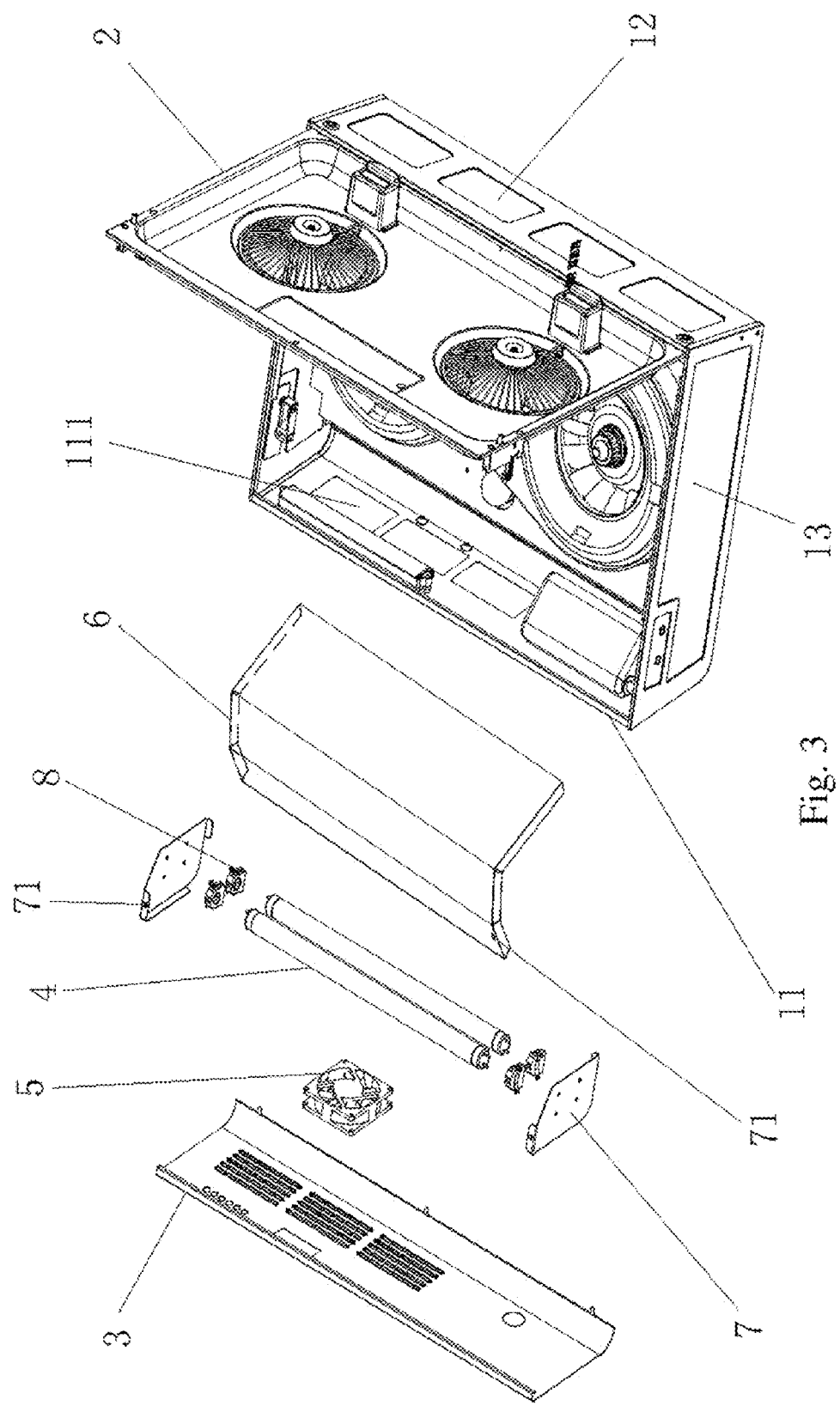
FIG. 3 depicts an exploded view of the oil-smoke extractor shown in FIG. 1.

Referring to FIGS. 1, to 3, an oil-smoke extractor according to one embodiment of the present invention includes a housing 1 defining an opening (not labeled) at a lower section thereof and a bottom plate 2 detachably positioned in the opening. The housing 1 includes a front plate 11, a rear plate 12, a pair of opposite side plates 13 and a top plate 14. An electric motor (not shown), a wind wheel 9 and an automatic cleaning device (not shown) are properly arranged in a receiving space jointly enclosed by the housing 1 and the bottom plate 2. The top plate 14 is formed with an oil-smoke discharging outlet 18. The bottom plate 2 is provided with a pair of oil-smoke pumping inlets 21.

Figure 4:
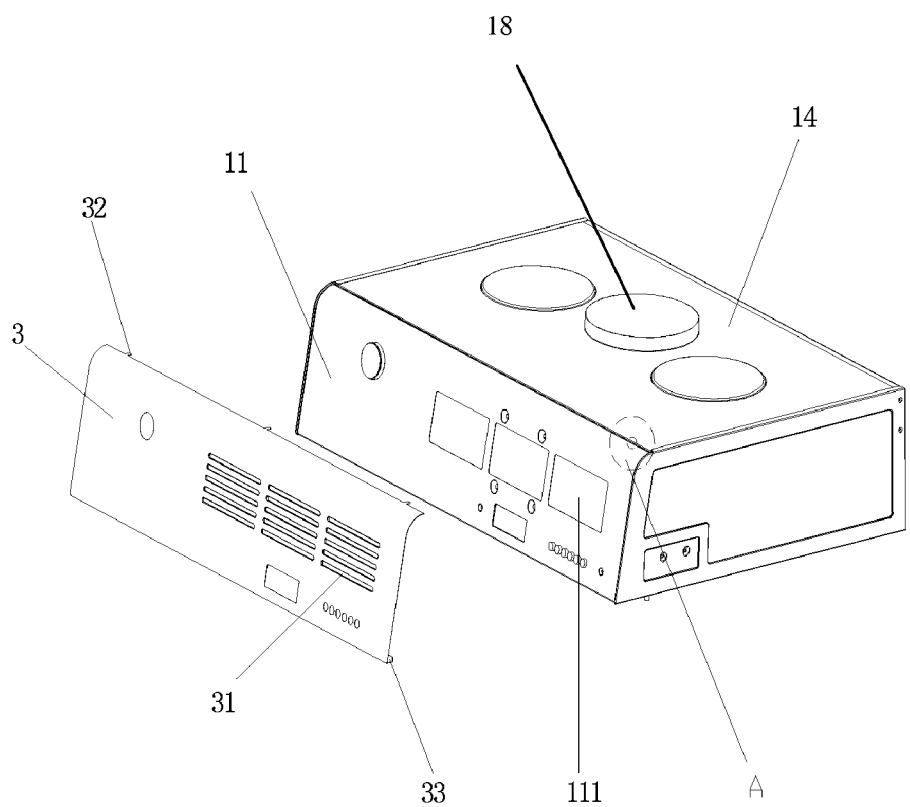
FIG. 4 depicts another exploded view of the oil-smoke extractor shown in FIG. 1, showing a decorative board of the oil-smoke extractor being removed from the housing.

Referring particularly to FIG. 3, the oil-smoke extractor in accordance with one embodiment of the present further includes a sterilization and deodorization device properly positioned in the receiving space. The sterilization and deodorization device includes an axial flow fan 5, two nano photocatalyst lamps 4, a sterilization lampshade 6, two lamp supports 7 and a pair of lamp holders 8. The two lamp supports 7 are fixed to the front plate 11 via welding or other ordinary means well known in the art. The lamp holders 8 are fixed on the lamp supports 7, respectively. Screws are inserted into threaded holes 71 defined in the sterilization lampshade 6 and the lamp supports 7, so as to fix the sterilization lampshade 6 and the lamp supports 7 together. The two nano photocatalyst lamps 4 are disposed between the two lamp holders 8. The sterilization lampshade 6 is fixed to the lamp supports 7. As shown in FIG. 4, three air holes 111 aligning with the nano photocatalyst lamps 4 are defined in the front plate 11. The axial flow fan 5 is mounted on the front plate 11, aligning with one of the air holes 111. In the illustrated embodiment, the front plate 11, the top plate 14, the lamp supports 7 and the sterilization lampshade 6 jointly defines an air treatment chamber (not labeled) to treat the kitchen air. It should be noted that, in accordance with other embodiments of the present invention, the amount of the air holes 111 can also be adjusted in accordance with different actual requirements.

According to another embodiment of the present invention, the air treatment chamber can also be corporately defined by the front plate 11, the lamp supports 7 and the sterilization lampshade 6.

Figure 5:
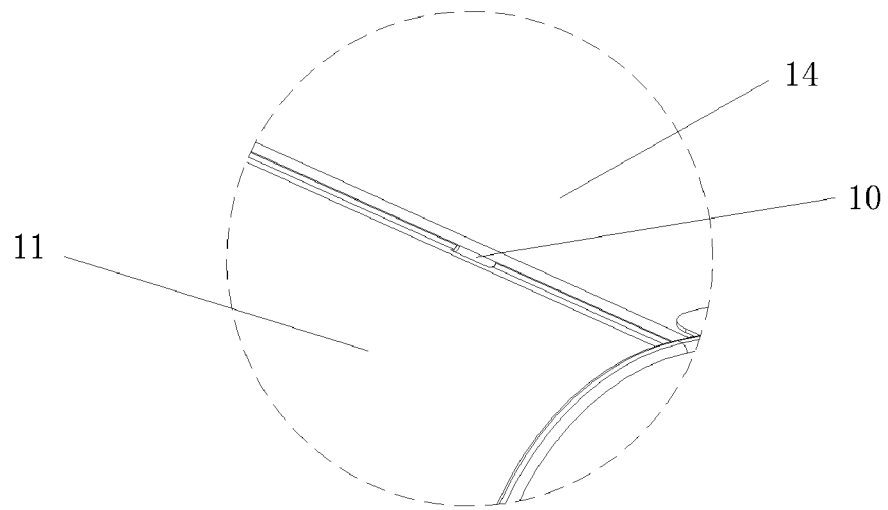
FIG. 5 depicts an enlarged view of circled part A in FIG. 4.

Referring particularly to FIGS. 4 and 5, the smoke extractor according to one embodiment of the present invention further includes a decorative board 3 removably assembled to the front plate 11. The decorative board 3 defines three rows of air slots 31 corresponding to the air holes 111 in the front plate 11. A number of protrusions 32 are formed at upper edge of the decorative board 3. A mounting recesses 33 is defined at a lower edge of the decorative board 3. A number of mounting slits 10 are defined at the conjunction of the front plate 11 and the top plate 14. In assembly, the lower edge of the front plate 11 is situated on the mounting recess 33 and the protrusions 32 are inserted into corresponding mounting slits 10. Alternatively, according to other embodiments of the present invention, the amount and arrangement of the air slots 31 can also be adjusted according to the arrangement of the air holes 111.

The nano photocatalyst lamp 4 is a lamp having a wavelength of 365 nmUV. Outer surface of the lamp 4 is coated with a layer of nano photocatalyst $TiO_2$ or covered with a layer of glass-fiber fabric implanted with nano photocatalyst $TiO_2$.

In the oil-smoke extractor in accordance with one embodiment of the present invention, when the oil-smoke extractor stops operating, the axial flow fan 9 and the at least one nano photocatalyst lamp 4 are powered and begin to operate. The kitchen air flows into and out of the oil-smoke extractor though the air slots 31 and the air holes 111. The nano photocatalyst lamp 4 can effectively and quickly kill the bacteria in the kitchen air and purify the environment. Therefore, peculiar smell in the kitchen air is eliminated and breeding of bacteria is also effectively prevented.

While the present invention has been illustrated by the above description of the preferred embodiment thereof, while the preferred embodiment has been described in considerable detail, it is not intended to restrict or in any way limit the scope of the appended claims to such details. Additional advantages and modifications within the spirit and scope of the present invention will readily appear to those skilled in the art. Therefore, the present invention is not limited to the specific details and the illustrative examples shown and described.

What is claimed is:

1. An oil-smoke extractor, comprising
    a housing comprising a front plate, a rear plate, a pair of side plates and a top plate, the housing defining an opening at a lower section thereof;
    a bottom plate detachably seated in the opening, the bottom plate and the housing jointly defining a receiving space; and
    a sterilization and deodorization device received in the receiving space, the sterilization and deodorization device comprising an axial flow fan, at least one nano photocatalyst lamp, a sterilization lampshade, two lamp supports and at least one pair of lamp holders;
    wherein the two lamp supports are fixed on the front plate, the at least one pair of lamp holders are respectively fixed on the lamp supports, the sterilization lampshade are fixed to the lamp supports, at least one nano photocatalyst lamp is disposed between the lamp holders, a plurality of air holes aligning with the at least one nano photocatalyst lamp is defined in the front plate and the axial flow fan is positioned corresponding to one of the air holes in the front plate.

2. The oil-smoke extractor of claim 1, wherein the oil-smoke extractor comprises a decorative board, the decorative board defines a plurality of air slots corresponding to the air holes.

3. The oil-smoke extractor of claim 2, wherein the decorative board forms a plurality of protrusions at upper edge thereof and a mounting recess at lower edge thereof, a plurality of mounting slits is defined in the conjunction of the front plate and the top plate, the low edge of the housing is seated in the mounting recess, and the protrusions are respectively inserted into the mounting slits.

4. The oil-smoke extractor of claim 1, wherein the at least one nano photocatalyst lamp is a lamp having a wavelength of 365 nmUV, outer surface of the lamp is coated with a layer of nano photocatalyst $TiO_2$ or covered with a layer of glass-fiber implanted with nano photocatalyst $TiO_2$.

5. An oil-smoke extractor, comprising:
    a housing comprising a front plate, the front plate defining a plurality of air holes;
    a bottom plate detachably assembled to the housing, the housing and the bottom plate jointly defining a receiving space; and
    a sterilization and deodorization device seated in the receiving space, the sterilization and deodorization device comprising:
        a pair of lamp supports fixed to the front plate;
        a pair of lamp holders secured to the lamp supports, respectively;
        at least one nano photocatalyst lamp disposed between the lamp holders;
        a sterilization lampshade fixed to the lamp supports; and
        an axial flow fan corresponding to one of the air holes of the front plate disposed in the receiving space.

6. The oil-smoke extractor of claim 5, wherein the oil-smoke extractor further comprises a decorative board, the decorative board defines a plurality of air slots corresponding to the air holes defined in the front plate.

7. The oil-smoke extractor of claim 6, wherein the decorative board forms a plurality of protrusions at upper edge thereof and defines a mounting recess at a lower edge thereof, a plurality of mounting slits are provided at the conjunction of the front plate and the top plate, in assembly, the lower edge of the front plate is seated in the mounting recess and the protrusions are inserted into corresponding mounting slits.

8. The oil-smoke extractor of claim 5, wherein the at least one nano photocatalyst lamp is a lamp having a wavelength of 365 nmUV, outer surface of the lamp is coated with a layer of nano photocatalyst $TiO_2$ or is covered with a layer of glass-fiber implanted with nano photocatalyst $TiO_2$.

* * * * *